(12) United States Patent
Jordanov

(10) Patent No.: US 6,522,984 B1
(45) Date of Patent: Feb. 18, 2003

(54) INSTANT POLE-ZERO CORRECTOR FOR DIGITAL RADIATION SPECTROMETERS AND THE SAME WITH AUTOMATIC ATTENUATOR CALIBRATION

(75) Inventor: Valentin T. Jordanov, Durham, NH (US)

(73) Assignee: Canberra Industries, Inc., Meriden, CT (US)

(*) Notice: Subject to any disclaimer, the term of this patent is extended or adjusted under 35 U.S.C. 154(b) by 114 days.

(21) Appl. No.: 09/607,715

(22) Filed: Jun. 30, 2000

Related U.S. Application Data

(60) Provisional application No. 60/142,199, filed on Jul. 1, 1999, and provisional application No. 60/145,846, filed on Jul. 27, 1999.

(51) Int. Cl.⁷ .............................................. G06F 19/00
(52) U.S. Cl. ........................................ 702/107; 378/91
(58) Field of Search ................................. 702/70, 71, 75, 702/76, 189, 190, 191, 126, 183, 67, 107; 330/107, 109, 292, 144; 378/91; 455/67.1; 327/131

(56) References Cited

U.S. PATENT DOCUMENTS

| | | | |
|---|---|---|---|
| 4,658,216 A | * 7/1983 | Goulding et al. | ............ 327/131 |
| 4,866,400 A | 9/1989 | Britton et al. | |
| 5,321,849 A | * 5/1991 | Lemson | ...................... 455/67.1 |
| 5,774,522 A | * 8/1996 | Warburton | .................... 378/91 |
| 5,872,363 A | 2/1999 | Bingham et al. | |

OTHER PUBLICATIONS

Nowlin et al., "Elimination of Undershoot in the Operation . . . ", Rev. Sci. Instr., vol. 36, 12, pp. 1830–1839, 1965, US.
Cover et al., "Automated Regulation of Critical Parameters . . . ", IEEE Trans. Nucl. Sci., vol. 29, No. 1, op 609–613, 1982, US.
Jordanov et al., "Digital Synthesis of Pulse Shapes in Real . . . ", Nucl. Instr. and Meth., A345, pp 337–345, 1994, NL.
Jordanov, "Digital Techniques for Real Time Pulse Shaping . . . " Nucl. Instr. and Meth., A353, pp 261–264, 1994, NL.
Jordanov, "Deconvolution of Pulses from a Detector–Amplifier . . . ", Nucl. Instr. and Meth., pp. 592–594, 1994, NL.

* cited by examiner

*Primary Examiner*—Marc S. Hoff
*Assistant Examiner*—Mohamed Charioui
(74) *Attorney, Agent, or Firm*—John H. Crozier

(57) ABSTRACT

In one preferred embodiment, method and apparatus for instant pole-zero correction for digital radiation spectrometers. In another embodiment, there are provided method and apparatus for instant pole-zero correction for digital radiation spectrometers with automatic attenuator calibration.

4 Claims, 16 Drawing Sheets

INSTANT POLE-ZERO CORRECTOR FOR DIGITAL RADIATION SPECTROMETERS AND THE SAME WITH AUTOMATIC ATTENUATOR CALIBRATION

This application claims benefit of 60/142,199 filed Jul. 1, 1999 and 60/145,846 filed Jul. 27, 1999.

BACKGROUND OF THE INVENTION

1. Field of the Invention

The present invention relates to pole zero correction generally and, more particularly, to a novel instant pole-zero corrector for digital radiation spectrometers and the same with automatic attenuator calibration.

2. Background Art

The problem of pole-zero cancellation was recognized at the early development of charge sensitive preamplifiers for radiation spectroscopy. See, for example, C. H. Nowlin and J. L. Blankenship, "Elimination of Undesirable Undershoot in the Operation and Testing of Nuclear Pulse Amplifiers", Rev. Sci. Instr., Vol 36, 12, pp 1830–1839, 1965. The charge sensitive preamplifier produces a voltage step that is proportional to the collected charge from the radiation detector. The charge-to-voltage conversion is achieved by using a capacitor as a negative feedback element of a low noise amplifier. The capacitor accumulates the input charge, which leads to constant increase of the output voltage of the amplifier. Supply voltages limit the output dynamic range of the preamplifier. Therefore, the total charge accumulated across the feedback capacitor is also limited.

To maintain a linear operation of the preamplifier, it is necessary to discharge (reset) periodically the feedback capacitor or to bleed the capacitor charge continuously through a resistor connected in parallel with the feedback capacitor. The first type of preamplifier is known as a "reset" feedback charge sensitive preamplifier. The pole-zero cancellation is associated with the second type of preamplifier often referred to as a "resistive" feedback preamplifier. Hereafter in this description, this type of preamplifier will be simply called a "preamplifier". A simplified diagram of the preamplifier is shown in FIG. 1.

When radiation interact with the detector a short current pulse I(t) is produced. The response of the preamplifier to this current is Vp(t). A simple analysis of the circuit can be carried out in the frequency domain –I(s), Vp(s). The input impedance of the preamplifier is $$Z_i = \frac{1}{C_i\left(s + \frac{1}{\tau_i}\right)},$$

The feedback impedance is $$Z_f = \frac{1}{C_f\left(s + \frac{1}{\tau_f}\right)},$$

where $\tau_f = C_f R_f$. For simplicity it is assumed that the gain A of the amplifier is frequency-independent.

The transfer function of the preamplifier can be found by solving the following system of equations:

$$I(s) = I_i(s) + I_f(s) \tag{1}$$

$$I_1(s) \cdot Z_1(s) = -\frac{V_p(s)}{A} \tag{2}$$

$$I_i(s) \cdot Z_i(s) - V_p(s) = I_f(s) \cdot Z_f(s) \tag{3}$$

where, $I_i(s)$ and $I_f(s)$ are the currents flowing through the input impedance and the feedback impedance respectively.

After solving the system of equations (1) to (3) the transfer function is found to be:

$$H_p(s) = \frac{V_p(s)}{I(s)} = \frac{1}{\frac{1}{A \cdot Z_i(s)} + \frac{A+1}{A \cdot Z_f(s)}} \tag{4}$$

After substituting the expressions for $Z_i(s)$ and $Z_f(s)$ into (4), $H_p(s)$ can be expressed as:

$$H_p(s) = \frac{\frac{A}{A+1}}{\left(C_f + \frac{C_i}{A+1}\right)\left(s + \frac{1}{\frac{R_i R_f}{R_i + \frac{R_f}{A+1}}\left(C_f + \frac{C_i}{A+1}\right)}\right)} \tag{5}$$

Let $$C_p = \left(C_f + \frac{C_i}{A+1}\right) \tag{6}$$

$$R_p = \frac{R_i R_f}{R_i + \frac{R_f}{A+1}} \tag{7}$$

$$\tau_p = R_p C_p \tag{8}$$

$$k_p = \left(\frac{A}{A+1}\right)\frac{1}{C_p} \tag{9}$$

Using the new variables the preamplifier transfer function can be rewritten as:

$$H_p(s) = \frac{k_p}{s + \frac{1}{\tau_p}} \tag{10}$$

Equation (10) represents a single real pole transfer function similar to the transfer function of a low-pass filter. For large gain of the amplifier (A>>)

$$\tau_p \approx \tau_f = R_f C_f \text{ and } k_p \approx \frac{1}{C_f}.$$

From equation (10) the impulse response of the preamplifier can be found. The inverse Laplace transform gives the well known exponential response:

$$h_p(t) = k_p e^{-\frac{t}{\tau_p}} \tag{11}$$

The response of the preamplifier to a detector current I(t) is given by the convolution integral:

$$v_p(t) = \int_u^t I(\lambda) h_p(t-\lambda) d\lambda = \int_u^t I(\lambda) k_p e^{-\frac{t-\lambda}{\tau_p}} d\lambda \quad (12)$$

One important property of this response is that if the current has a finite duration, than the signal at the output of the preamplifier will decay exponentially after the current becomes zero. The decay time constant of the tail of the signal is the same as the decay time constant of the impulse response. FIG. 2 illustrates such response. The preamplifier response to a finite current signal can be easily derived from Equation (12). First, the detector current is defined as:

$$I(t) = \begin{cases} I(t) & 0 \le t < T_c \\ 0 & t < 0, t \ge T_c \end{cases} \quad (13)$$

From Equations (12) and (13) the response of the preamplifier for $t > T_c$ can be written as:

$$v_p(t) = \int_0^{T_c} I(\lambda) k_p e^{-\frac{t-\lambda}{\tau_p}} d\lambda = k_p e^{-\frac{t}{\tau_p}} \int_0^{T_c} I(\lambda) k_p e^{\frac{\lambda}{\tau_p}} d\lambda \quad (14)$$

where, the integral $$\int_0^{T_c} I(\lambda) k_p e^{\frac{\lambda}{\tau_p}} d\lambda$$

is a constant. Therefore, for $t > T_c$ the preamplifier signal exponentially decays with the same time constant as given by the impulse response. FIG. 2 shows the preamplifier response to a finite detector current.

Due to various constraints such as noise performance and stability requirements, the preamplifier time constant is usually large. In order to optimize signal to noise ratio and to meet certain throughput requirements it is necessary to "shorten" the preamplifier exponential pulse. Traditionally, this is done using a CR differentiation network (CR high-pass filter). FIG. 3 shows a preamplifier-CR differentiator configuration.

The CR differentiation network plays an important role in analog pulse shapers. Digital pulse processors also benefit from digitizing short exponential pulses—better utilization of ADC resolution, reduced pile-up losses, and simple gain control. The pole-zero cancellation is an important procedure for both analog and digital pulse processing systems.

When exponential pulses pass through a CR differentiation, circuit the output signal is bipolar. The combined transfer function of the preamplifier-differentiator configuration can be written as:

$$H(s) = \frac{k_p}{s + \frac{1}{\tau_p}} \cdot \frac{s}{s + \frac{1}{\tau_d}} = k_p \cdot s \cdot \frac{1}{s + \frac{1}{\tau_p}} \cdot \frac{1}{s + \frac{1}{\tau_d}} \quad (15)$$

where $\tau_d = C_d R_d$. The impulse response can be obtained from the inverse Laplace transformation:

$$h(t) = k_p \frac{1}{\frac{1}{\tau_d} - \frac{1}{\tau_p}} \left( \frac{1}{\tau_d} e^{-\frac{t}{\tau_d}} - \frac{1}{\tau_p} e^{-\frac{t}{\tau_p}} \right) \quad (16)$$

If the ratio between the time constants of the preamplifier and the differentiator is $$w = \frac{\tau_p}{\tau_d},$$

then Equation (16) can be rewritten as:

$$h(t) = k_p \frac{w}{w-1} \left( e^{-\frac{t}{\tau_d}} - \frac{1}{w} e^{-\frac{t}{\tau_p}} \right) = k_p \frac{w}{w-1} e^{-\frac{t}{\tau_d}} - \frac{1}{w-1} \left( k_p e^{-\frac{t}{\tau_p}} \right) \quad (17)$$

Equation 17 indicates that the response of the preamplifier-differentiator can be expressed as difference of two responses. Both responses represent single real pole systems. The second term in equation (17) is the response of the preamplifier attenuated by a factor of $$\frac{1}{w-1}.$$

Thus, a single pole response with time constant $\tau_d$ can be achieved by simply adding a fraction $$\frac{1}{w-1}$$

of the preamplifier signal to the output of the differentiation network.

FIG. 4 shows a basic pole-zero cancellation circuit. The preamplifier signal is applied to a high-pass filter network and a resistive attenuator (e.g. trimpot). The high-pass filter output and the attenuated preamplifier signal are added together and than passed to the pulse shaper. In early designs the analog adder was built using passive components—resistors. Although simple, the resistive adder has a major drawback—its impedance will change with the change of the trim-pot. As a result the pole-zero adjustment inevitably affects the high-pass filter time constant. This drawback can be overcome by using active components to sum the signals from the high-pass filter and the attenuator.

In early development of the spectroscopy pulse shapers, the pole-zero adjustment was performed manually. The manual adjustment is done using an oscilloscope as an inspection tool for under or overshoot of the differentiated and shaped pulse. The operator uses his/her visual judgment to properly adjust the pole-zero. The manual adjustment can be time consuming and often requires special skills to perform the task.

An automatic approach for pole-zero correction is described in U.S. Pat. Nos. 4,866,400 and 5,872,363, both titled AUTOMATIC POLE-ZERO ADJUSTMENT CIRCUIT FOR AN IONIZING RADIATION SPECTROSCOPY SYSTEM. The automatic setup combines a circuit similar to one described in Cover et al., "Automated Regulation of Critical Parameters and Related Design Aspects of Spectroscopy Amplifiers with Time-Invariant Filters", IEEE Trans. Nucl. Sci., Vol 29, No. 1, pp 609–613, February 1982. This circuit estimates whether the signal (after differentiation and pulse shaping) has an undershoot or an overshoot. In addition to the undershoot/overshoot estimator, the automatic pole-zero circuit comprises a control logic, a digitally controlled attenuator (MDAC), and current summer using an operational amplifier. This automatic pole-zero adjustment uses consecutive iterations. This is, it works on the principle of error-trial. In order to adjust the pole-zero, a large number of measurements are needed. The iterative algorithm can be time consuming, requiring a large number of measurements. In addition, the termination of the iterative process may result in miss-adjustments. Due to the requirement for a large number of pulse measurements, this iterative pole-zero adjustment scheme can be a major limitation when the detector counting rates are very low. The algorithms of the above patents are based on trail-error sequence and do not assume any knowledge or measurement of the parameters of the system.

Accordingly, it is a principal object of the present invention to provide a pole-zero corrector for digital radiation spectrometers that is essentially instant.

A further object of the present invention is to provide pole-zero corrector for digital radiation spectrometers that includes automatic attenuator calibration.

Another object of the invention is to provide such correctors that are easily implemented.

Other objects of the invention, as well as particular features, elements, and advantages thereof, will be elucidated in, or be apparent from, the following description and the accompanying drawing figures.

SUMMARY OF THE INVENTION

The present invention achieves the above objects, among others, by providing, in one preferred embodiment, method and means for instant pole-zero correction for digital radiation spectrometers. In another embodiment, there is provided method and means for instant pole-zero correction for digital radiation spectrometers with automatic attenuator calibration.

BRIEF DESCRIPTION OF THE DRAWING

Understanding of the present invention and the various aspects thereof will be facilitated by reference to the accompanying drawing figures, submitted for purposes of illustration only and not intended to define the scope of the invention, on which.

DETAILED DESCRIPTION OF THE PREFERRED EMBODIMENTS

Figure 1:
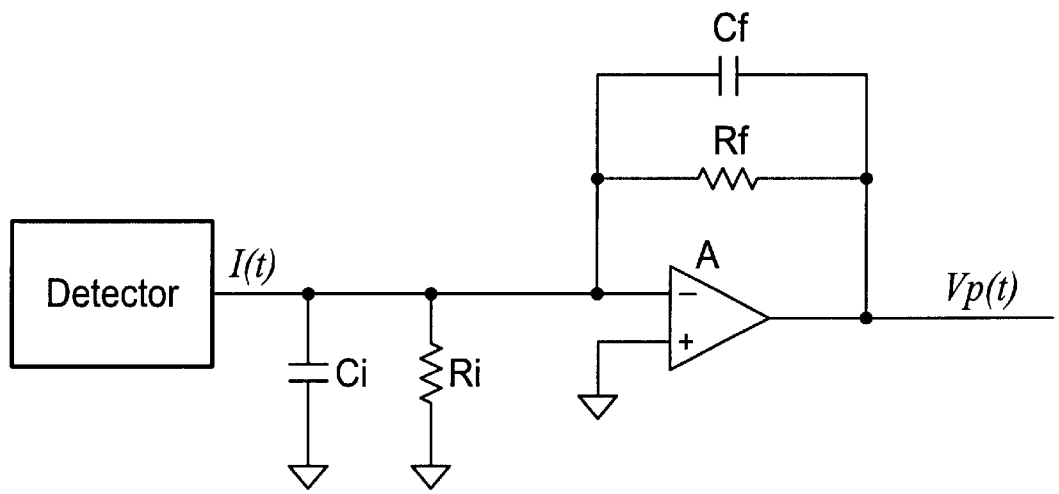
FIG. 1 is a schematic diagram of a resistive feedback preamplifier.
Figure 2:
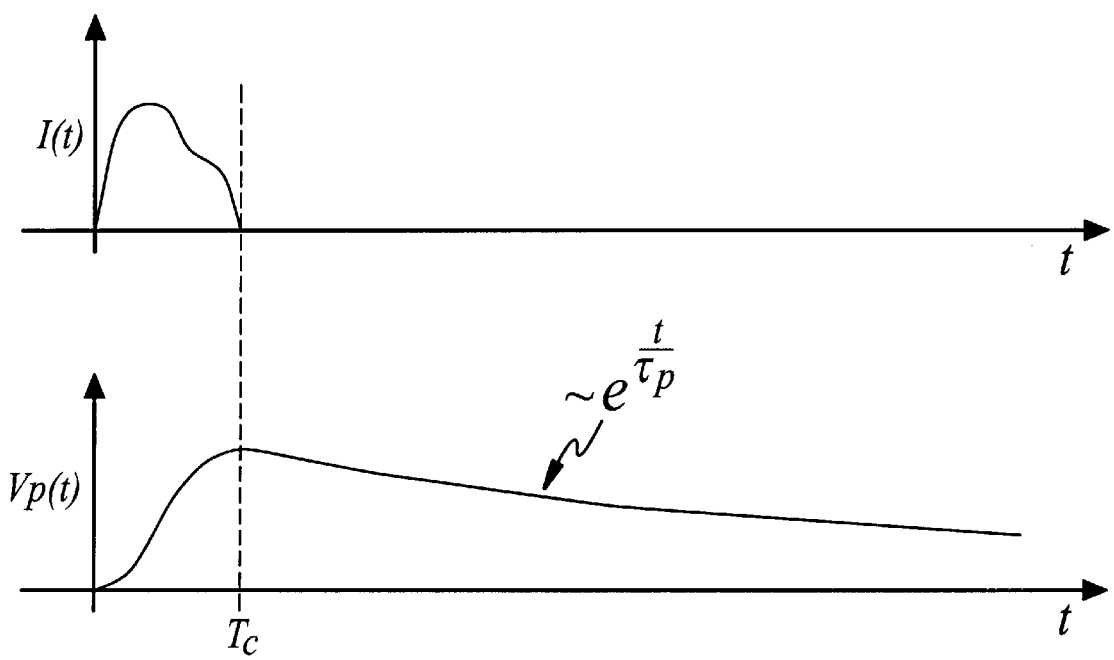
FIG. 2 shows response of a preamplifier to a finite detector current.
Figure 3:
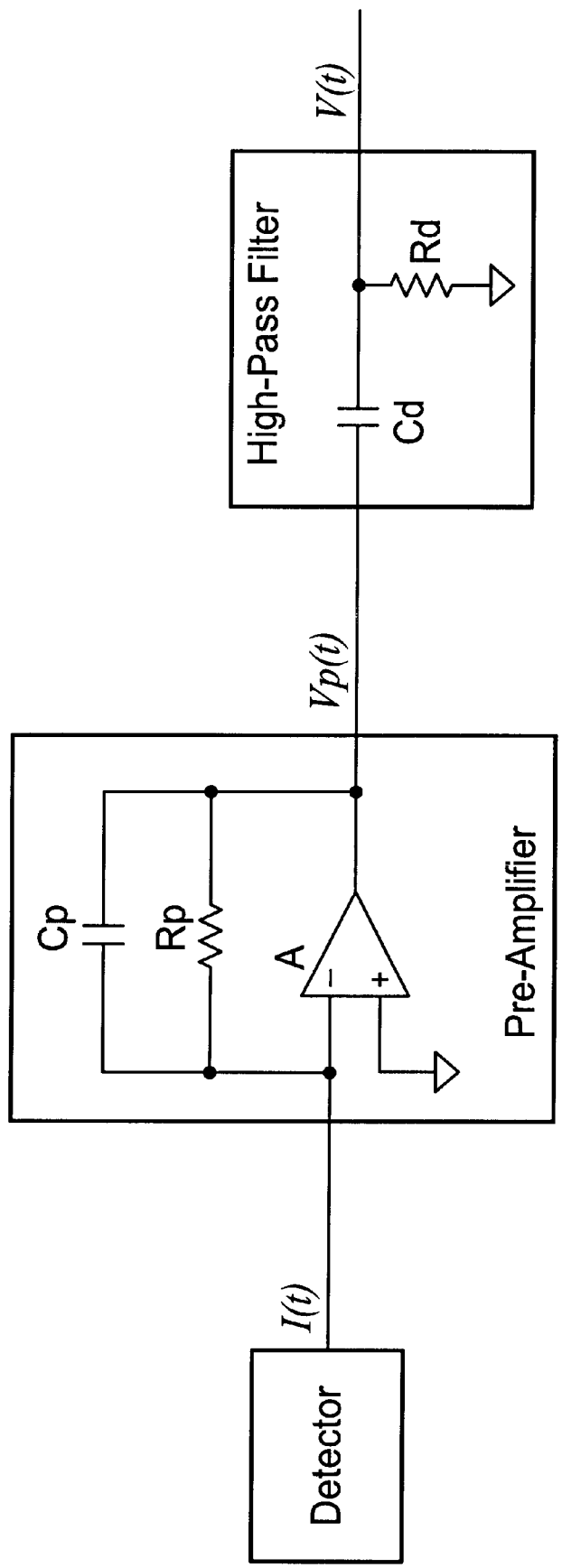
FIG. 3 is a block/schematic diagram of a preamplifier-CR differentiator configuration.

Reference should now be made to the drawing figures, on which similar or identical elements are given consistent identifying numerals throughout the various figures thereof, and on which parenthetical references to figure numbers direct the reader to the view(s) on which the element(s) being described is (are) best seen, although the element(s) may be seen also on other views.

With the development of the digital pulse processing systems it has become possible for a different approach to adjust the pole-zero. The digital shapers, such as described in V. T. Jordanov and G. F. Knoll, "Digital Synthesis of Pulse Shapes in Real Time for High Resolution Spectroscopy", *Nucl. Instr. and Meth.*, A345, pp. 337–345, 1994; V. T. Jordanov "Digital Techniques for Real Time Pulse Shaping in Radiation Measurements", *Nucl. Instr. and Meth.*, A353, pp. 261–264, 1994; and V. T. Jordanov, "Deconvolution of Pulses from a Detector-Amplifier Configuration", *Nucl. Instr. and Meth.*, A351, pp. 592–594, 1994, requires a well-defined time constant of the CR differentiation network. In addition, the responses of the discrete pulse-shaping networks are well known and their inverse response is fully predictable. The digital signal processing/analysis also allows measurement of the preamplifier time constant and an instant pole-zero cancellation. The analysis of the discrete pulse waveforms makes also possible the automatic detection of the presence of a reset type charge-sensitive preamplifier.

Figure 5:
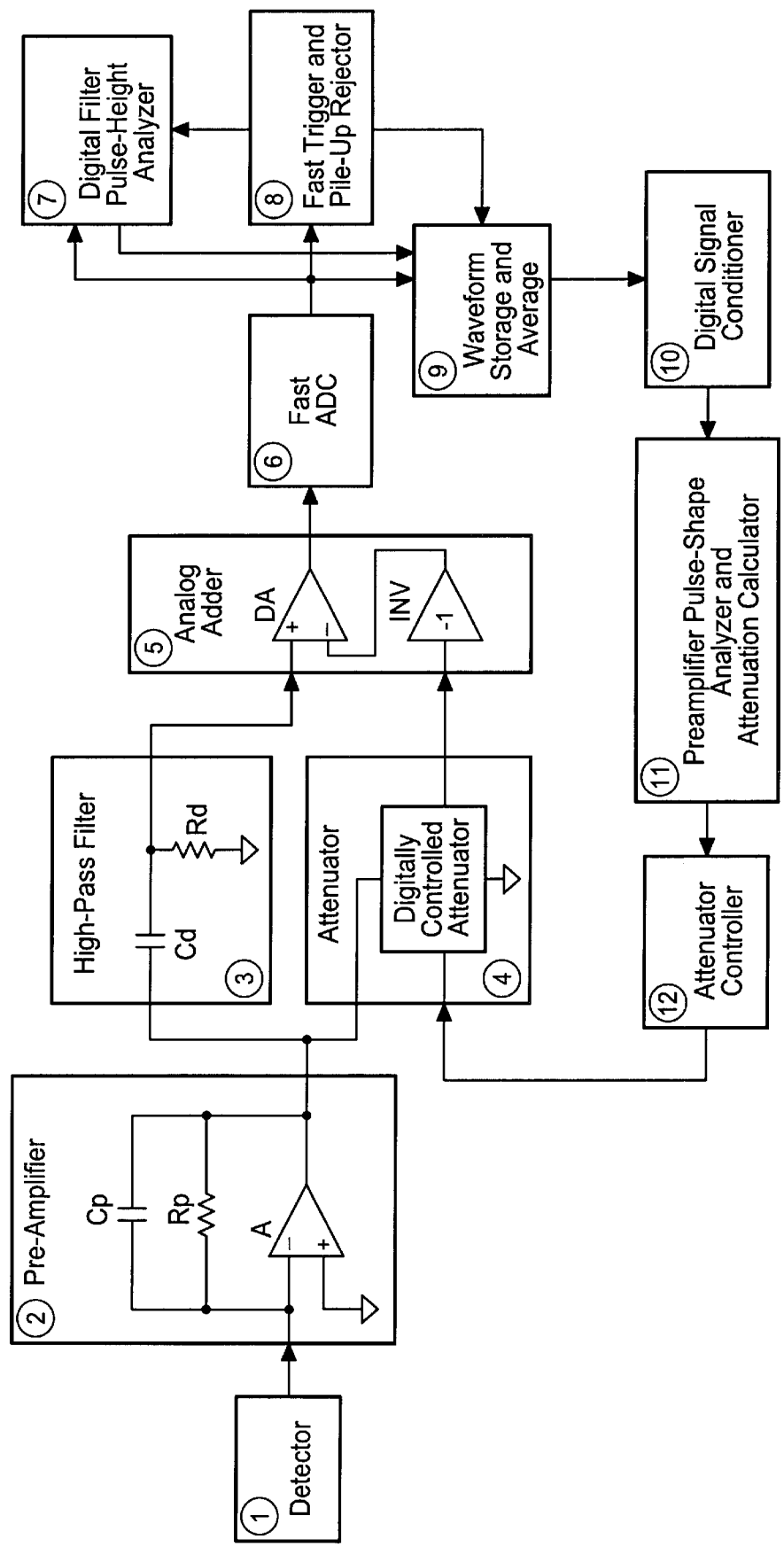
FIG. 5 is a block diagram of an instant pole-zero corrector according to the present invention.

The instant pole-zero corrector may be employed by different pulse processor arrangements including both analog and digital pulse processing units. FIG. 5 depicts a typical case of digital pulse processor using analog attenuator and digital fast discriminator. The detector (1) signal is sensed by a charge-sensitive preamplifier (2). The output of the preamplifier is applied to a CR high-pass filter (3) and digitally controlled attenuator (4). Analog adder (5) adds the signals from the high pass filter and the attenuator. The signal from the adder is digitized by a fast ADC (6). The discrete waveform from the ADC is applied to a digital spectroscopy filter (7) and a fast trigger and pile-up rejector (8) and to a waveform storage and average unit (9). The storage/average unit may also accept the digitally shaped signal from the digital filter (7) (connection shown with dashed line). The fast discriminator and pile-up rejector is connected to the storage/average unit. The output of the storage/average unit is applied to a digital signal conditioner (10). The digital signal conditioner is connected to a preamplifier pulse-shape analyzer (11). The pulse shape analyzer provides data to an attenuator controller (11). The output of the controller is applied to the control input of the attenuator (4).

Figure 6:
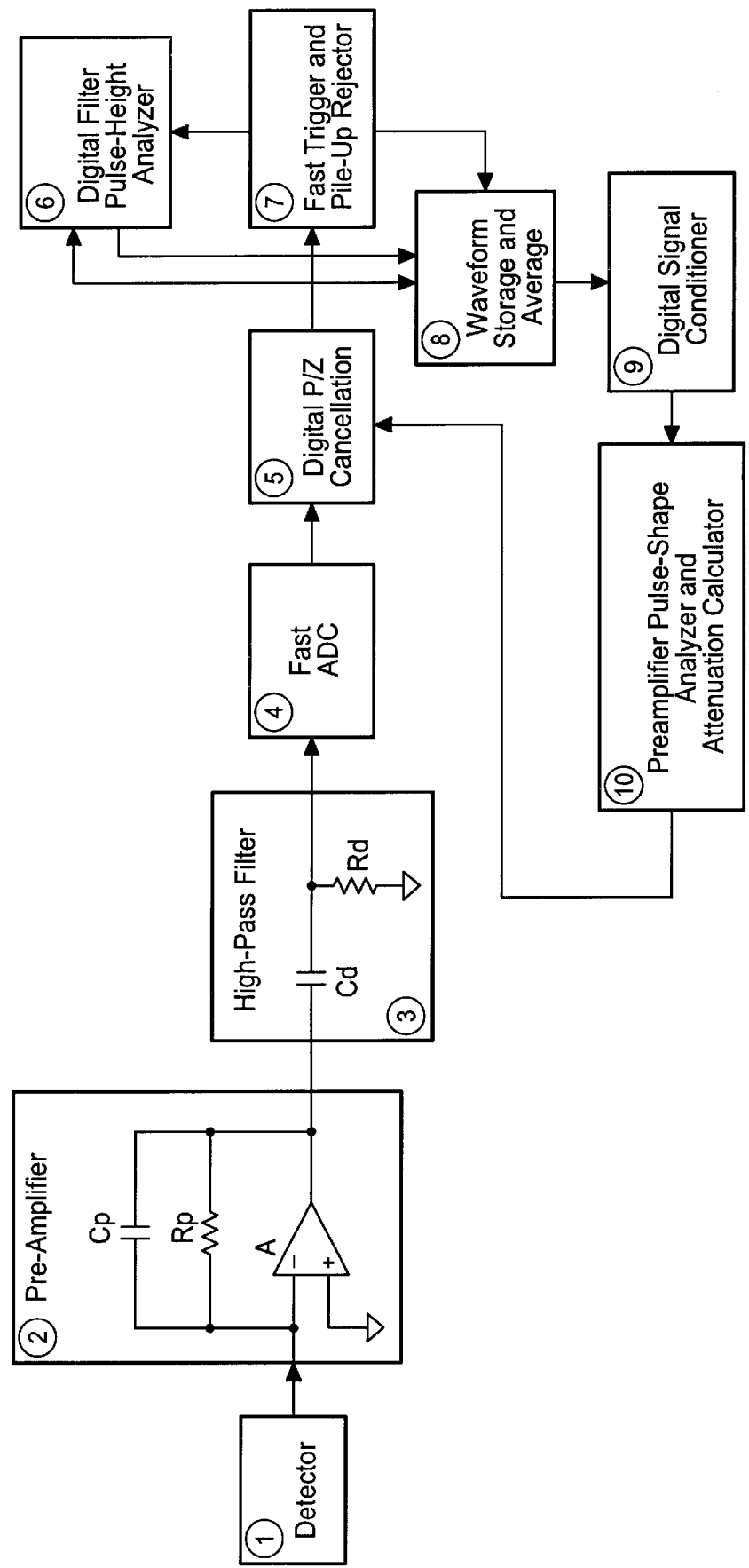
FIG. 6 is a block/schematic diagram of an instant pole-zero corrector using digital pole-zero cancellation.

FIG. 6 is a block diagram of an instant pole-zero corrector, according to the present invention, that uses a digital pole-zero cancellation circuit. A recursive digital pole-zero circuit has been described in the above *Nucl. Instr. and Meth.* references. This circuit operates in real time and requires only two parameters. The first parameter is the time constant of the CR differentiator which is fixed and known in advance. The second parameter is the preamplifier time constant that is determined in the process of instant pole-zero correction.

Figure 7:
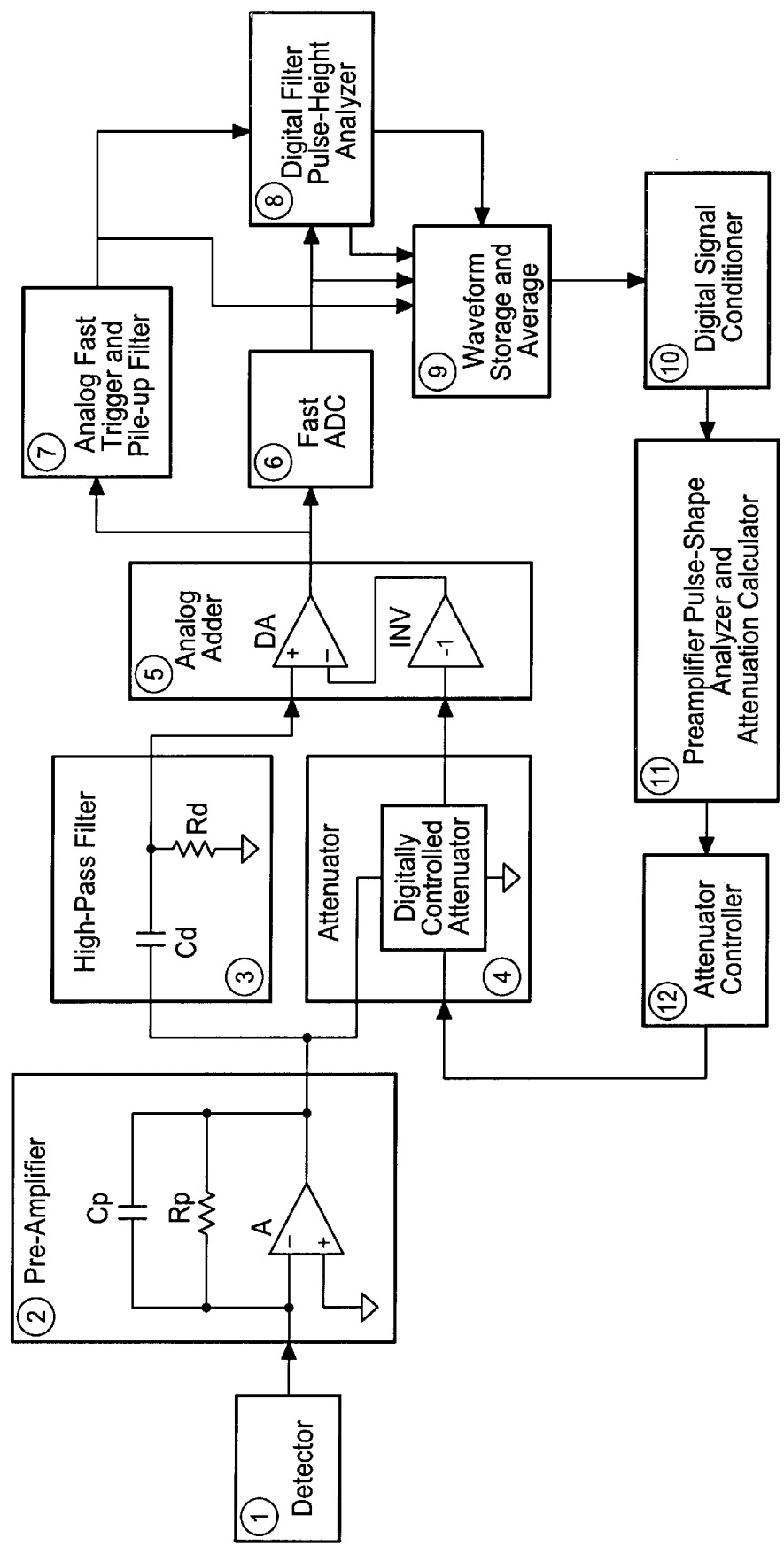
FIG. 7 is a block/schematic diagram of an instant pole-zero corrector with analog trigger.

There are a number of possible modifications of the block diagrams that will have the same functionality as the block diagrams depicted in FIGS. 5 and 6. For instance, an analog trigger (fast discriminator) can be used to control the waveform acquisition and pile-up rejection. FIG. 7 shows an example of an instant pole-zero corrector that is functionally equivalent to the configuration in FIG. 5.

Other arrangements allow sampling and storage of waveforms that contain the preamplifier response. These may include schemes with direct digitization of the preamplifier signal, digitization of analog signal pre-shaped using networks with known parameters, using separate ADC, etc. Different arrangements for the waveform storage trigger exist. Units such as low level discriminators (digital and analog) or differential discriminators may serve the same function as the trigger and the pile-up rejector depicted in FIGS. 5, 6, 7.

A common feature between all circuits discussed above is the algorithm that they implement in order to achieve an instant pole-zero correction. The essential task of instant pole-zero algorithm is to determine the time constant of the preamplifier.

Figure 8:
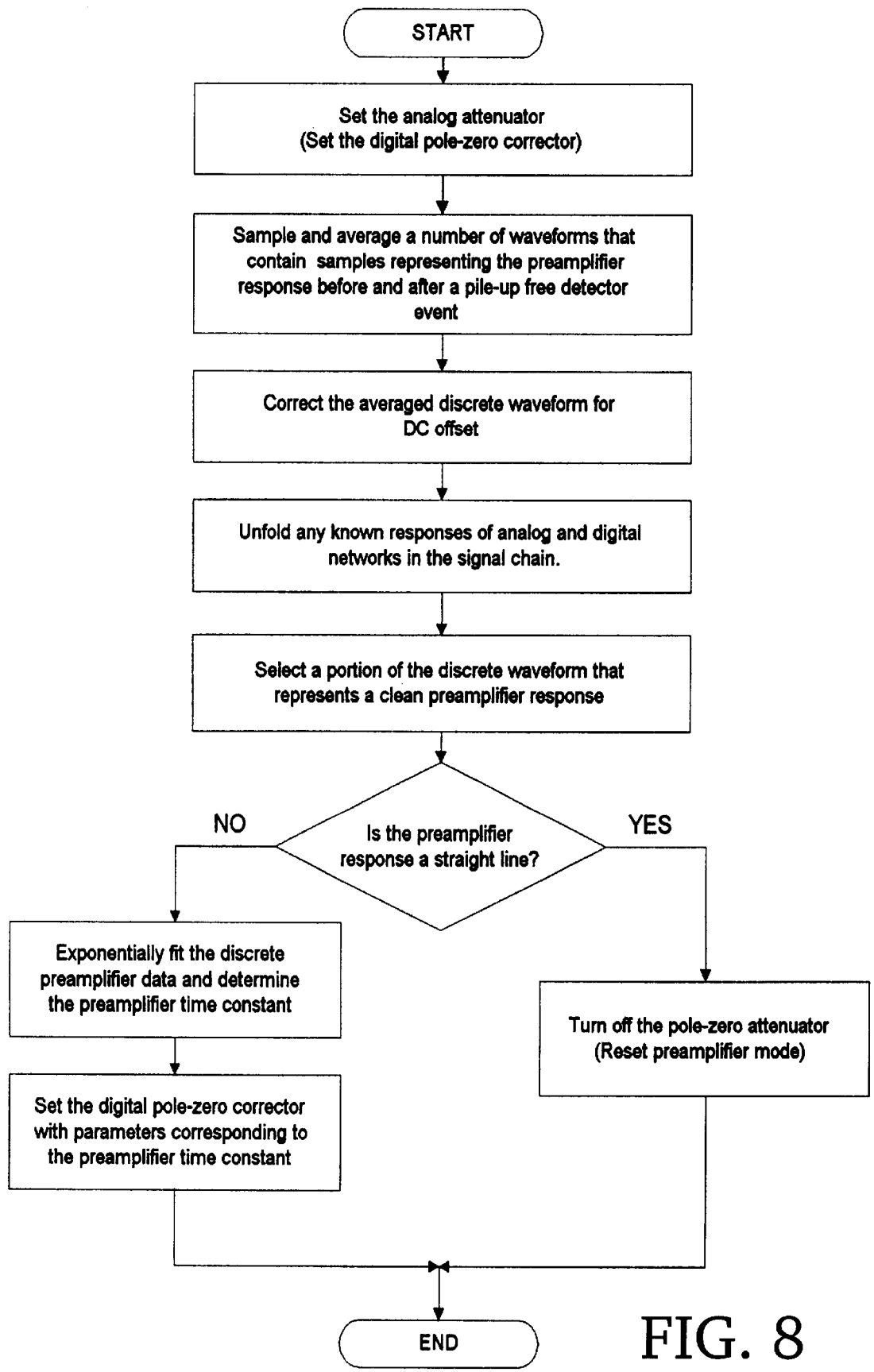
FIG. 8 illustrates the algorithm for the instant pole-zero corrector.
Figure 9:
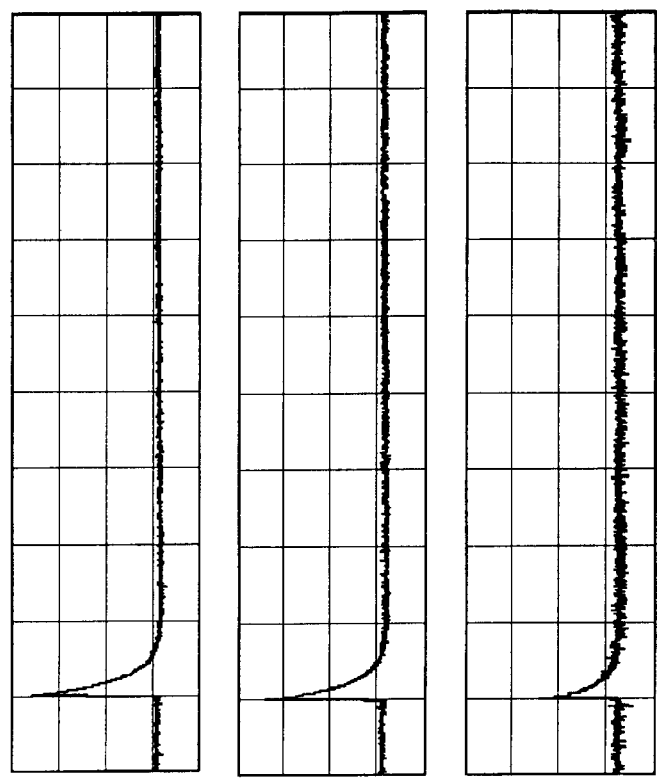
FIG. 9 shows waveforms of discrete signals taken directly after the fast ADC of FIG. 5.

The instant pole-zero corrector operates according to the algorithm illustrated in FIG. 8. This algorithm represents a generalized model including the arrangements in FIGS. 5, 6, and 7. First step of the algorithm is to set the analog attenuator or the digital pole-zero cancellation circuit before storing discrete waveforms. The digital waveforms can be acquired at one or more attenuator settings—e.g., attenuator is turned off or the smallest attenuation is applied. Similarly, the digital pole-zero corrector can be turned off or can be set with known parameters. If waveforms are taken at different initial settings they can be combined in order to reduce statistical variations of sampled signals. After the initial settings of the P/Z cancellation elements a number of digitized waveforms can be acquired and averaged. The waveform storage is done in pretrigger fashion. That is, a certain number of samples preceding the detector event are stored along the samples after the detector event. The fast trigger and pile-up rejector controls the waveform storage. The pile-up pulse shapes are detected and excluded from averaging. FIG. 9 depicts few captured pulse waveforms that are added to an averaging sum.

Figure 10:
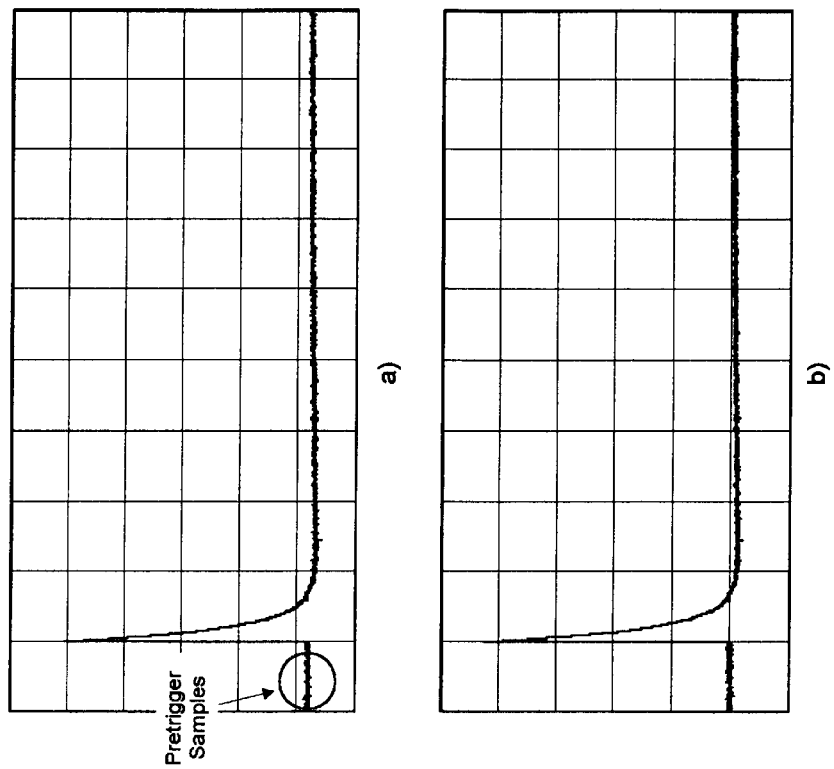
FIG. 10(a) shows the average preamplifier-discriminator response before DC offset correction.
FIG. 10(b) shows the average preamplifier-discriminator response after DC offset correction.

After a sufficient number of waveforms are acquired the averaged sum can be corrected for DC offset. The DC offset is estimated from the pretrigger samples. FIG. 10 shows the average preamplifier-differentiator response before and after DC offset correction. The samples used to estimate the DC offset are indicated with a circle.

After the DC correction, the algorithm in FIG. 8 performs analysis on the DC corrected pulse shape in order to determine the time constant of the preamplifier. This pulse shape analysis may include deconvolution of known analog and digital network impulse responses and selecting a portion of unfolded waveform that represents only the exponential response of the preamplifier. If the combined impulse responses of the analog and digital networks are finite (e.g., triangular/trapezoidal digital shaper) or with very short time constant than the deconvolution process can be omitted. In this case, the selection of the samples representing the preamplifier response depends on the total width of the combined impulse response of the analog and digital networks following the preamplifier plus some guard time to account for the short time scale unknown responses.

Figure 11:
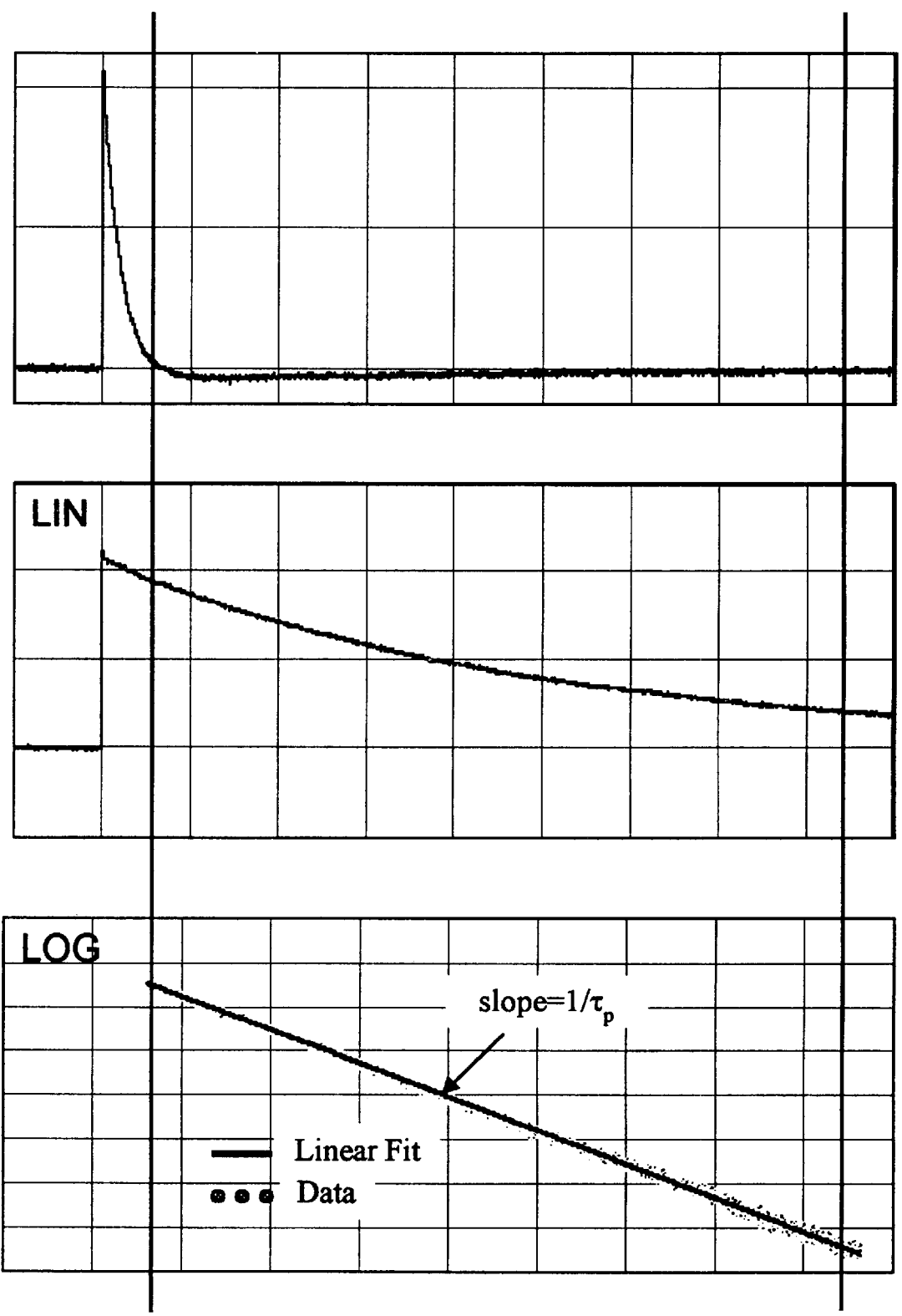
FIG. 11 shows the deconvolution of the CR differentiator response and calculation of the preamplifier time constant.

After the undesired responses are removed and a portion of the discrete data set is selected, the preamplifier time constant can be obtained. FIG. 11 illustrates the process of unfolding the CR differentiator response from discrete data that represent the differentiator output signal. After the deconvolution of the CR differentiator response, sampled data are obtained that are the preamplifier response. A portion of these data is selected to determine the preamplifier time constant. In this particular case, a logarithm is taken from the selected data and least means square linear fit is applied. The slope of the fitting line gives the time constant of the preamplifier.

Figure 12:
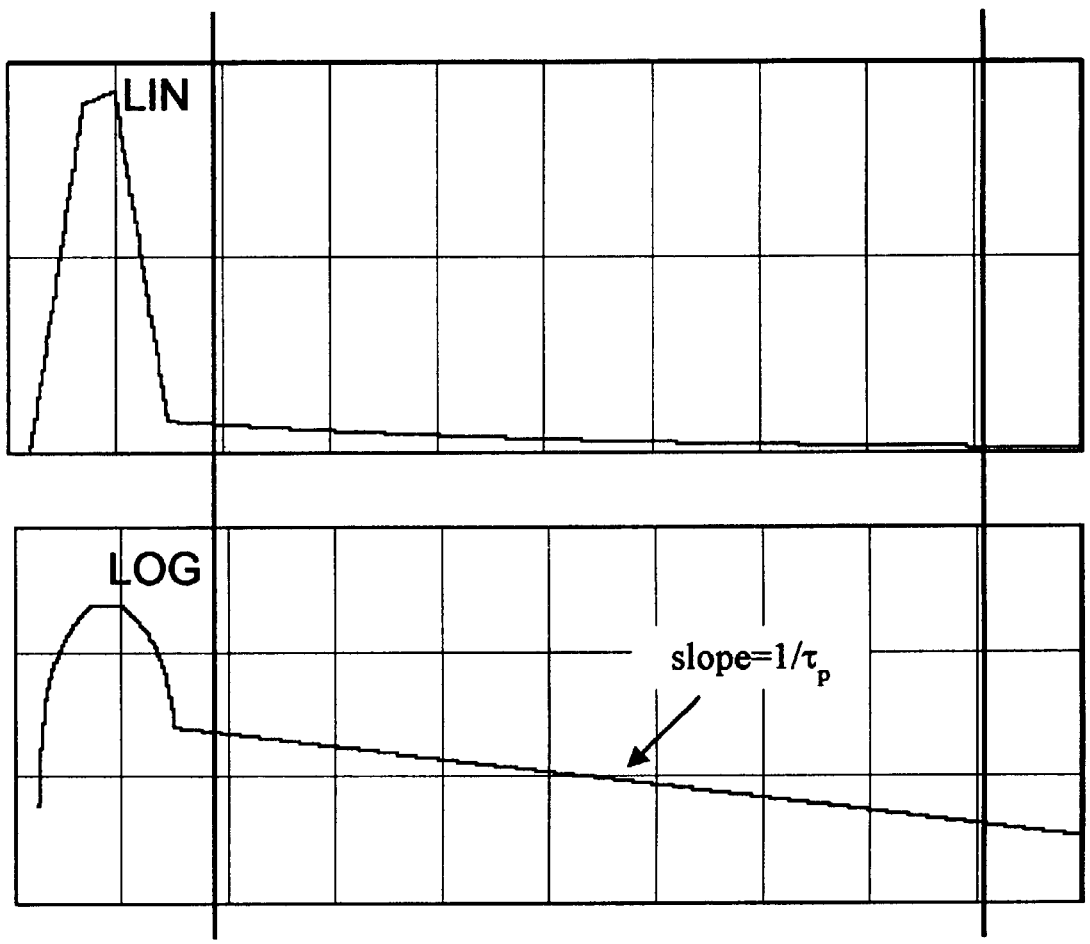
FIG. 12 shows the determination of the preamplifier time constant using discrete data after the digital pulse shaper.

The time constant of the preamplifier can be found from other discrete signals that contain the preamplifier response. FIG. 12 illustrates a case when a digitally shaped trapezoidal signal is analyzed. The preamplifier time constant is simply found from the tail of the sampled pulse. In this case the preamplifier response is convoluted with the finite impulse response of the differentiator-digital shaper network. Therefore, from Equation 14, the tail of the shaped pulse will have the same time constant as the preamplifier.

In a special case of reset preamplifier, the unfolded preamplifier signal (FIG. 11) or the tail of the shaped signal will be a straight line. This fact can be used to detect the presence of reset type preamplifier and to adjust (turn off) the pole-zero cancellation network.

Figure 4:
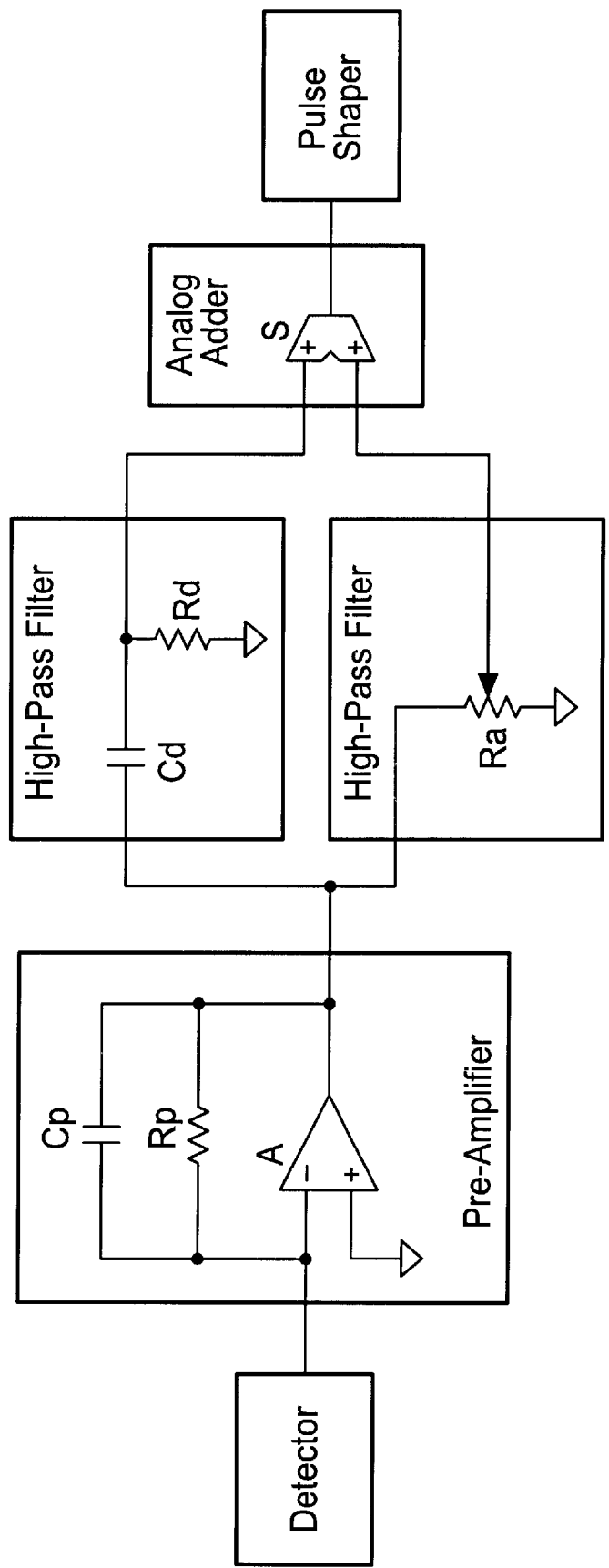
FIG. 4 is a block/schematic diagram of a basic pole-zero cancellation circuit.

Using the known time constant of the differentiator and the time constant of the preamplifier the attenuation coefficient of the analog attenuator (Equation 17) (FIG. 4) can be calculated. The attenuator is then adjusted with the calculated attenuation and an instant pole-zero cancellation is achieved. Similarly, the time constant of the preamplifier can be used to set a digital pole-zero attenuator. There is no need for further iterations in order to adjust the pole-zero.

The present invention further provides means and method for calculating and setting the digital pole-zero correction without prior knowledge of the attenuator calibration.

Figure 13:
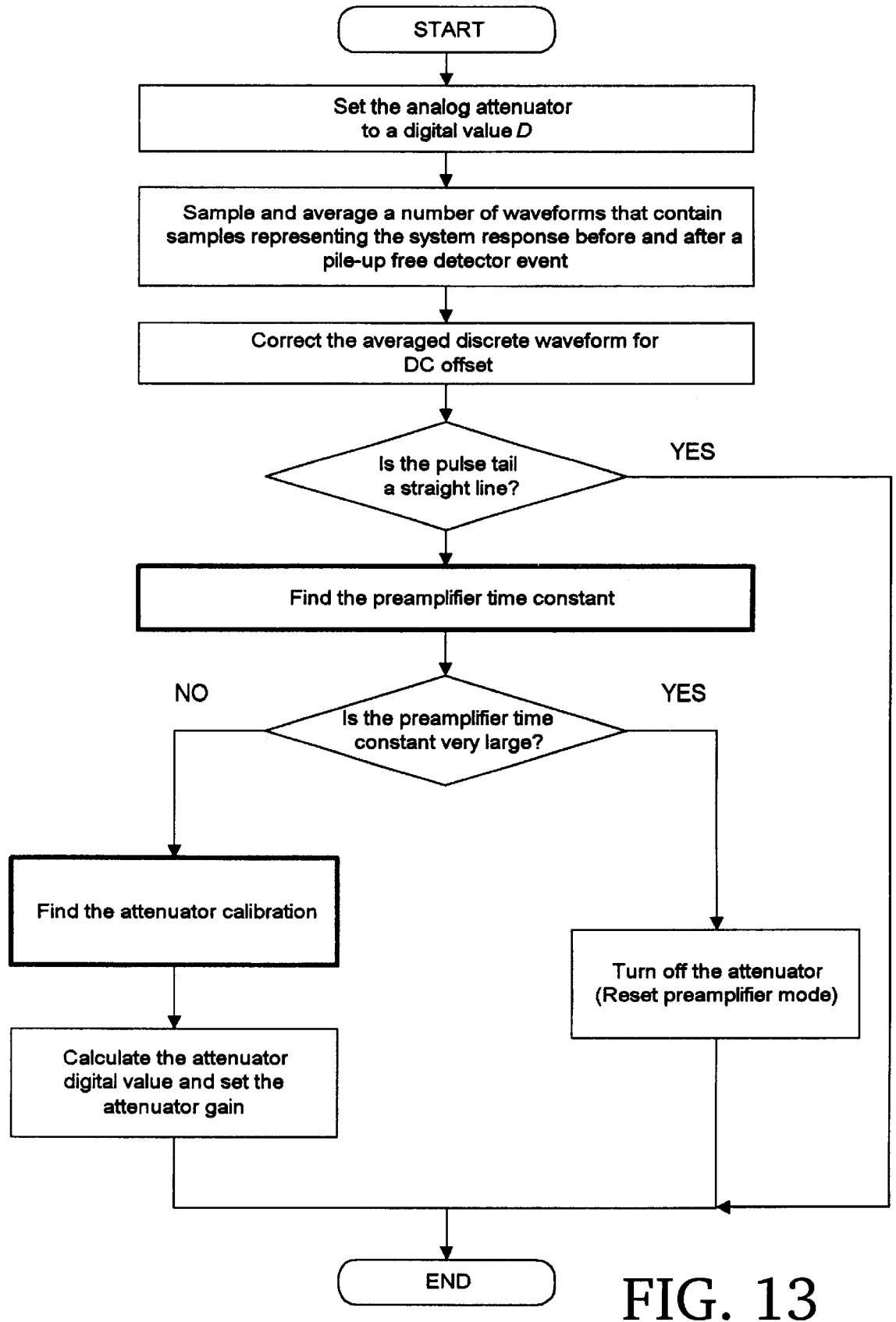
FIG. 13 is a flowchart of the method for setting pole-zero cancellation with automatic calibration of the attenuator.

FIG. 13 shows the flowchart of the method to set the pole-zero cancellation with automatic calibration of the attenuator. The algorithm begins with setting a digital value D to the attenuator and acquiring and averaging a number of pulse waveforms. The averaged waveform excludes waveforms that are subject to pile-up. The acquired data is a discrete waveform similar to the waveform in FIG. 14.

The next step is to determine the DC offset (if any) of the acquired waveform. Finding the average value of the pre-pulse data points (region 1 in FIG. 14) allows DC correction of the waveform. The pre-pulse data is selected slightly before the beginning of the shaped pulse in order to avoid false background data due to the timing jitter and timing walk of the acquired pulse waveforms. The averaged value obtained from pre-pulse data is subtracted from all waveform samples. The computational routines of the algorithm use this DC corrected data.

The slope of the waveform tail (region 3 in FIG. 14) is examined to determine whether or not it is straight line with zero slope and zero offset. If this is true it is not necessary to further process the data. The desired value d is equal to the preset value D and there is no need to change the preset value of the attenuator.

Figure 14:
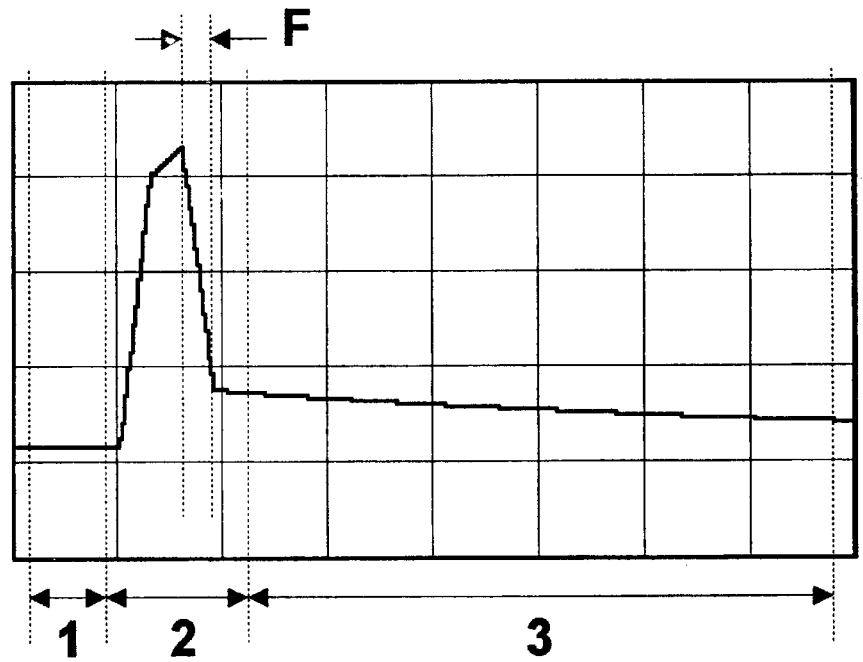
FIG. 14 is a waveform of averaged pulse events.
Figure 15:
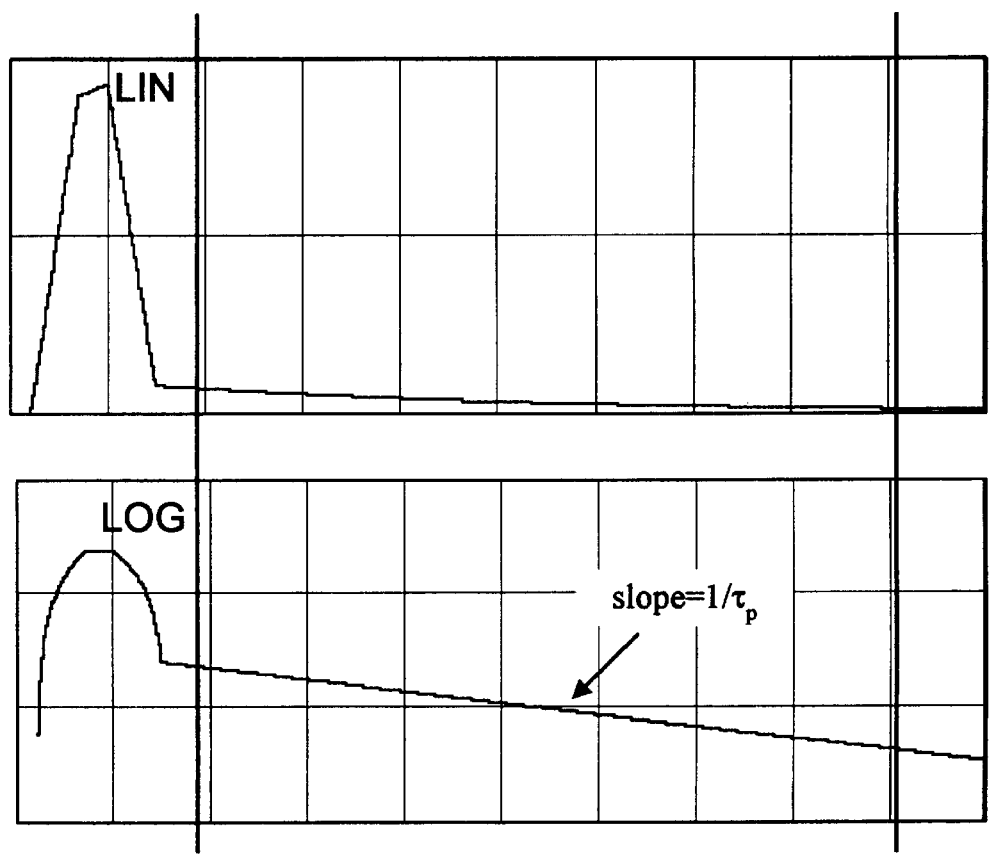
FIG. 15 shows the determination of the preamplifier time constant.

If the waveform tail has a slope different than zero then the computational routine for obtaining the preamplifier time constant is executed. The block of this routine is highlighted with a bold line in the flowchart. The preamplifier time constant is found from the tail data (data region 3, FIG. 14) of the sampled pulse waveform. This can be done, for example, by using an exponential fit to the data from the tail of the pulse. The fitting function can be obtained by using the least mean square (LMS) method. The preamplifier time constant is directly obtained from the exponential factor of the fitting function. FIG. 15 depicts an example to find the preamplifier time constant by taking a natural logarithm from the data and obtaining the preamplifier time constant from a linear data fit of the tail data points.

Another way to determine the preamplifier time constant is to search for it by repeatedly applying pole cancellation routine (low-pass filter impulse response deconvolution) as described in V. T. Jordanov, "Deconvolution of Pulses from a Detector-Amplifier Configuration", *Nucl. Inst. and Meth.* In the discrete time domain the removal of the low-pass filter response is achieved by a simple recursive procedure. Let u[n] be the discrete values of the signal that contains the low-pass response. The samples are spaced at equivalent periods of time $T_{clk}$. If the time constant of the low-pass filter is $\tau_{lp}$ then the recursive procedure to remove the low-pass filter response can be written as:

$$s[n]=(u[n]-u[n-1])\cdot N+u[n] \qquad (18)$$

where s[n] is the result free of the low-pass filter response and $$N = \frac{1}{e^{\frac{T_{clk}}{\tau_{lp}}} - 1}.$$

which is approximately equal to the preamplifier time constant expressed in number of clock samples. The procedure introduces a DC gain equal to N-1 but it has no significance for the obtained result.

Figure 16:
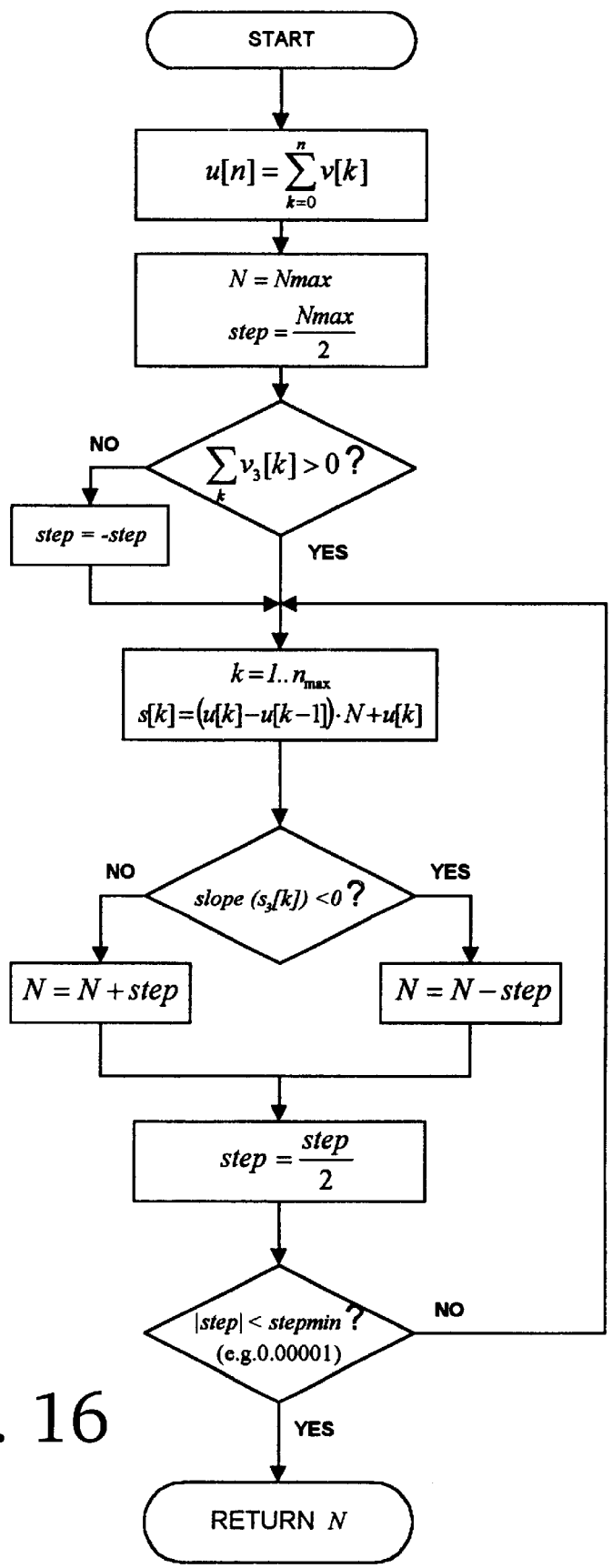
FIG. 16 is a flowchart of the procedure to determine the preamplifier time constant.

Using Equation (18), a simple iterative procedure can be employed to obtain the preamplifier time constant by testing computed values of N until the correct value is found. The procedure, shown in FIG. 16, works on either the data v[n] from the acquired waveform (FIG. 14) or on the data u[n] obtained after integration of v[n]. In the first case the tail (region 3 in FIG. 14) will become a straight line with zero slope and zero offset after the low-pass filter response is removed. In the second case, the tail becomes a straight line with zero slope but with non-zero offset that depends on the position of the zero at $$-\frac{1}{\tau_z}$$

in the transfer function. The second case may be useful when noise is present. In both cases, though, the criterion for cancellation of the preamplifier low-pass response is to obtain a straight line with zero slope in the tail region of the data.

Figure 17:
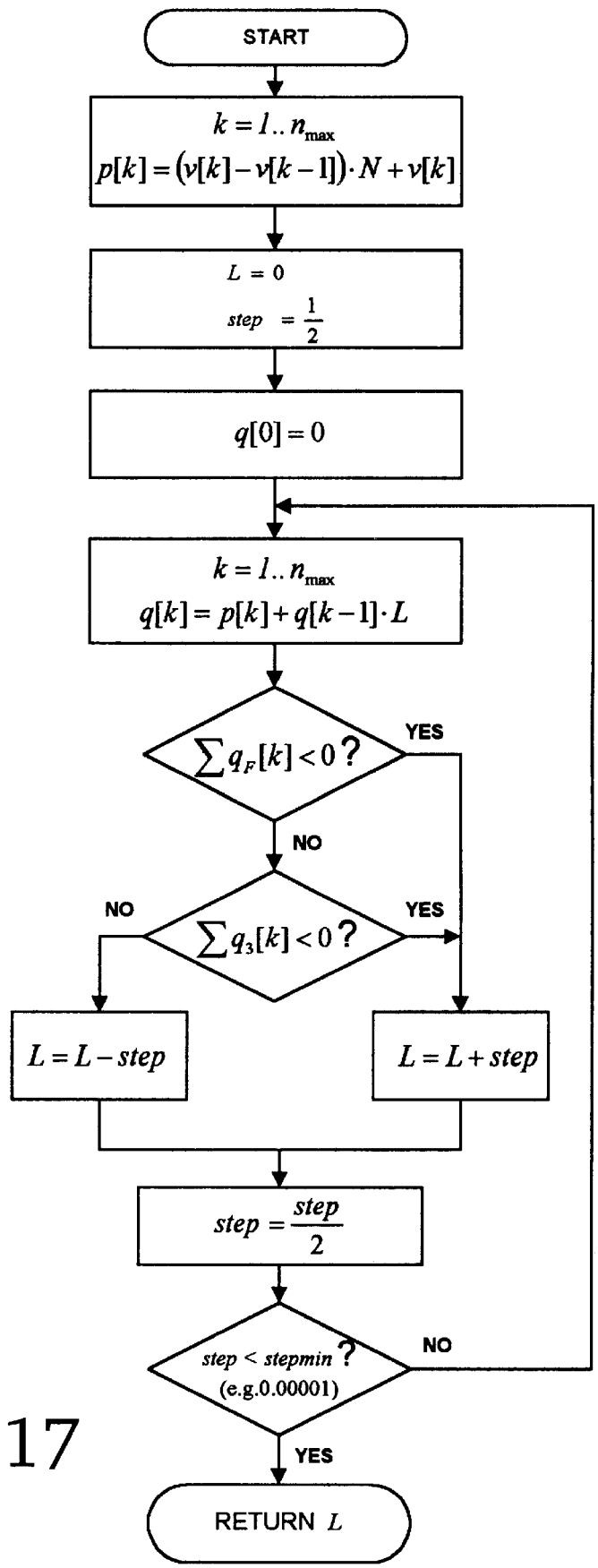
FIG. 17 is a flowchart of the procedure to determine the calibration of the digitally controlled attenuator.

The flowchart in FIG. 17 illustrates the procedure to cancel the preamplifier exponential response (low-pass filter pole) using the integrated waveform. At the beginning the acquired and averaged waveform v[n] is integrated resulting in a data set u[n]. In these flowcharts, the data from different regions of the waveform are indicated with a subscript corresponding to the numbering scheme of FIG. 14. For example $u_3[n]$ represents $n^{th}$ sample of the discrete signal from the tail of the waveform. The sample index for each region start with 0 at the beginning (left side) of the region. Samples without subscript belong to the entire waveform or its derivatives.

There are two variables that are used by the computational routine to determine the preamplifier time constant, N and step. The variable N is initially set to a very large number corresponding to a very large preamplifier time constant. The variable N can be set to a value corresponding to a preamplifier time constant of few hundreds of milliseconds. By iterative adjustment of N a computational cancellation of the preamplifier pole can be achieved. At each iteration the tail of the modified (pole cancellation) waveform is examined and N is modified using a stepping variable step. The stepping variable is initially set to half of the value of N so that it can be used in a successive approximation loop. After initializing the variables of the iteration procedure the tail of the original waveform u[n] is checked for under or overshoot in order to determine the direction of the iteration process. Changing the sign of the variable step changes the direction of the iteration process. At this point, the iteration process for finding N begins.

The iteration loop includes a pole cancellation recursive procedure that uses the integrated data u[n] and produces new data set s[n]. The slope of the tail of s[n] is examined in order to determine in which direction N has to change for the next iteration. The criterion for the iterative process to stop is to obtain a straight line with a zero slope in the tail portion of the pole-zero cancelled data s[n]. This will be achieved when the size of step becomes very small. When the absolute value of step becomes smaller than predetermined limit the iteration process stops and the procedure returns the value of N. The value of N is such that the pole of the preamplifier will be cancelled if N is used in the recursive procedure given by Equation (18). At the exit of the iterative process the time constant of the preamplifier is also calculated using N according to:

$$\tau_p = \frac{T_{clk}}{\ln\left(\frac{1+N}{N}\right)} \qquad (19)$$

After the preamplifier time constant is found, a check is performed on its magnitude (see flowchart in FIG. 13). If the time constant is very large then the preamplifier is considered a reset type preamplifier. The attenuator is turned off. This procedure represents an automatic detection of the type of preamplifier connected to the input of the radiation spectroscopy.

If a determination is made that the preamplifier is not a reset type a second iterative computational procedure is executed as highlighted in the flowchart in FIG. 13. This routine determines the calibration coefficient c of the digitally controlled analog attenuator.

Figure 18:
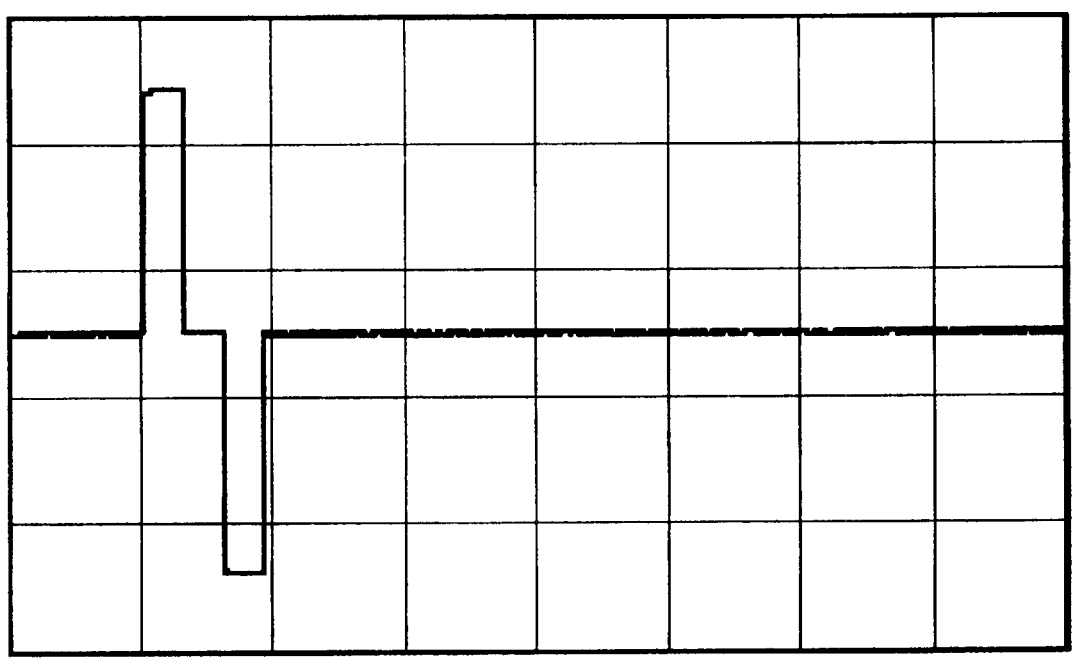
FIG. 18 is a waveform obtained from the sampled pulse waveform after applying a digital cancellation of the preamplifier response.

FIG. 17 shows the flowchart of the algorithm to find the calibration coefficient of the attenuator. This routine uses data p[n] generated by removing the preamplifier response of the averaged waveform v[n]. The recursive calculations use the parameter N obtained from the procedure that determines the preamplifier time constant. FIG. 18 depicts an example of p[n]. The exponential tail, as expected, is removed but due to the zero in the transfer function, the main pulse shape is differentiated. In order to calibrate the attenuator it is necessary to integrate this data. A true integration will result in a tail that is straight line with zero slope— equivalent to a DC offset. The DC offset in the tail region of data is proportional to the "zero" location at $$-\frac{1}{\tau_z}$$

of the transfer function. In other words, the DC offset is a function of the preset attenuator gain G and the differentiator time constant $\tau_d$. The zero in the transfer function (Equation (5)) can be canceled using a recursive routine:

$$q[n]=p[n]+q[n-1]\cdot L \qquad (20)$$

zero cancellation will be achieved when $$L = e^{-\frac{1}{\tau_z}T_{clk}} \qquad (21)$$

When the zero is cancelled the DC offset of the tail is removed. A simple recursive computational routine is used to determine the correct value of L by testing computed values of L until the correct value is found. The iteration process uses a variable step that controls the change of L in the successive approximation loop. The expected values for L are between 0 and 1. Therefore, the initial settings for L and step are 0 and 0.5 respectively. The conduction to terminate the iteration adjustment of L is to obtain a tail that is zero.

When L is very small, the signal is bipolar, similar to the waveform in FIG. 18 and the tail section is very close to a straight zero line. In this case, the waveform is examined for negative values in the region F of the pulse signal (FIG. 14). If the signal has negative values then L is incremented. Otherwise the tail part of the waveform is examined to determine if it is equal to zero and L is adjusted accordingly. As in the routine for determining the preamplifier time constant the loop is terminated when the step to increment/decrement L becomes very small. At the termination the routine returns the parameter L.

The attenuator calibration coefficient c can be determined as $$c = -\frac{1}{D}\ln(L) \cdot \frac{\tau_d}{\ln(L) \cdot \tau_d + T_{clk}} \qquad (22)$$

The pole-zero cancellation value d for the digitally controlled analog attenuator can be expressed as a function of L, N, D, $T_{clk}$, and $\tau_p$:

$$d = \frac{1}{c\left(\frac{\tau_p}{\tau_d} - 1\right)} = -D\ln(L) \cdot \tau_d + \frac{T_{clk}}{\ln(L) \cdot (\tau_p - \tau_d)} = \qquad (23)$$

$$-D\ln(L) \cdot \tau_d + \frac{T_{clk}}{\ln(L) \cdot \left(\frac{T_{clk}}{\ln\left(\frac{1+N}{N}\right)} - \tau_d\right)}$$

If $\tau_p$ and $\tau_d$ are much greater than $T_{clk}$ then the expression for d can be simplified avoiding logarithm calculations:

$$d \cong -D(L-1) \cdot \tau_d + \frac{T_{clk}}{(L-1) \cdot (T_{clk}(N-0.5) - \tau_d)} \qquad (24)$$

Equation (24) is suitable for implementation in embedded systems where mathematical computations are limited. The process of setting the pole-zero cancellation commences with the calculation of d from Equation (23) or Equation (24) and downloading d to the digitally controlled attenuator. At this point the automatic pole zero adjustment is completed.

Until now, we have assumed that the digital attenuation coefficient is a positive number. The algorithm described above is also applicable for negative values of D. This situation is useful if a digital, bipolar attenuator is used—for example, multiplying digital-to-analog converter connected in bipolar mode. The pulses are acquired with the digital attenuator set to the most negative value and they will always exhibit exponential undershoot tail. In this case the best signal-to-noise ratio for the sampled preamplifier component is achieved.

Figure 19:
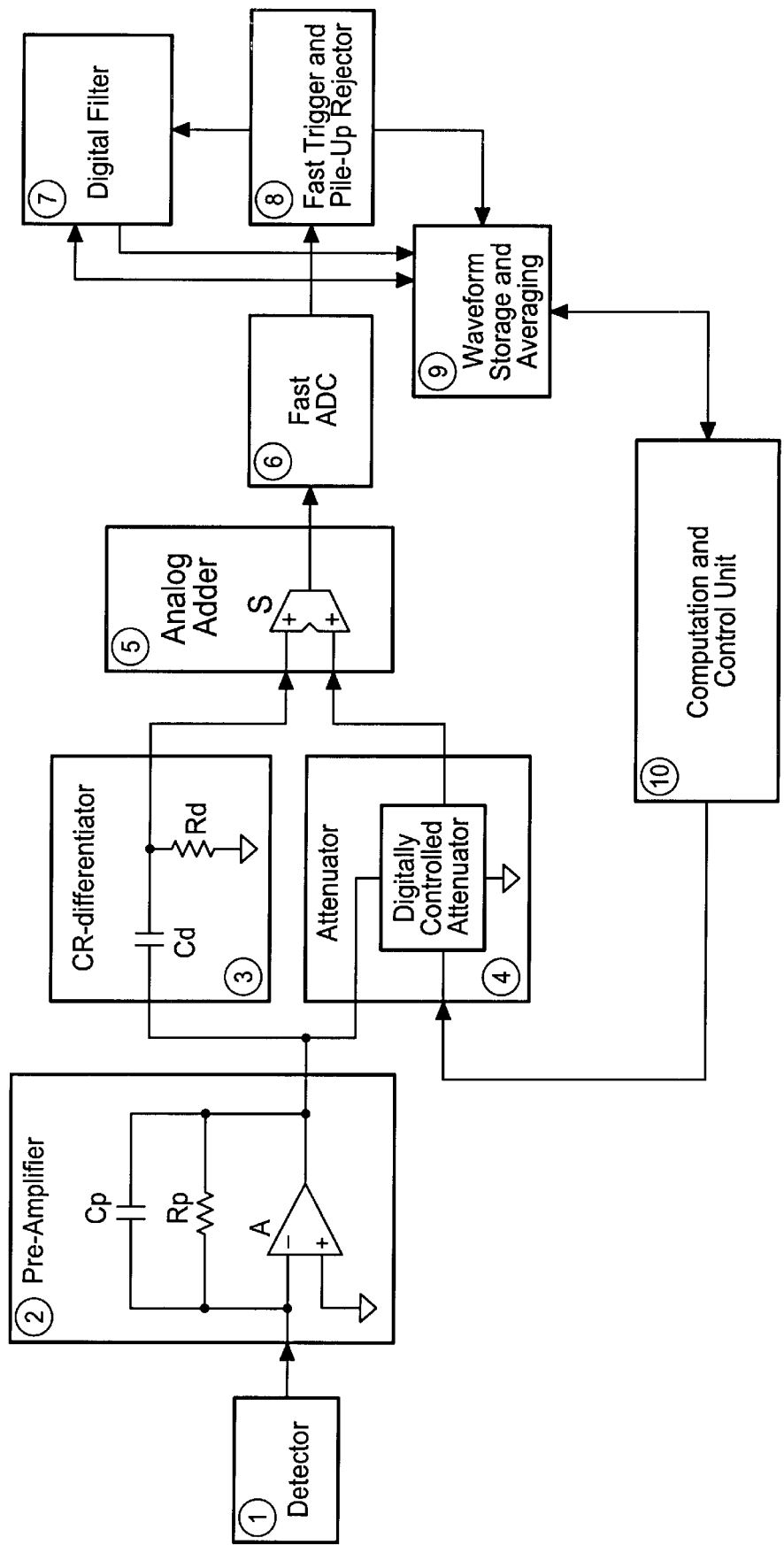
FIG. 19 is a block/schematic diagram of the circuit for instant pole-zero cancellation with attenuator calibration.

FIG. 19 shows the block diagram of the instant pole-zero cancellation circuit that implements the above described method. The detector (1) signal is sensed by a charge-sensitive preamplifier (2). The output of the preamplifier is applied to a CR differentiator (3) and digitally controlled attenuator (4). Analog adder (5) adds the signals from the CR-differentiator and the attenuator. The signal from the adder is digitized by a fast ADC (6). The discrete waveform from the ADC is applied to a digital spectroscopy filter (7) and to a fast trigger and pile-up rejector (8). The output of the digital shaper is applied to a storage and averaging unit (9). The storage/averaging unit may also accept the sampled signal directly from the ADC (6) (connection shown with a dashed line). The fast discriminator and pile-up rejector is also connected to the storage/averaging unit. The storage/averaging unit is connected to a computation and control unit (10). The output of the control unit is applied to the control input of the attenuator (4).

The signal from the preamplifier is differentiated (3) and added together with the signal from the attenuator (4). A fast ADC, normally in a continuous mode, digitizes the output of the adder. The pole-zero cancellation procedure starts with a command from the computational/control unit. First, the attenuator is loaded with a predefined digital value D. Next the computational/control unit enables the storage of the waveforms in the memory of (9). The storage/averaging unit is also controlled by the pile-up circuitry (8)—the waveforms with pile-up are disregarded. When a predetermined number of waveforms are acquired and the averaged discrete form is obtained the control unit initiates the pole-zero correction computational procedure.

The computation unit first corrects data for DC offset and then performs the computations and data manipulations as described above. The final result from these calculations is a digital value that is loaded to the digitally controlled attenuator.

In the embodiments of the present invention described above, it will be recognized that individual elements and/or features thereof are not necessarily limited to a particular embodiment but, where applicable, are interchangeable and can be used in any selected embodiment even though such may not be specifically shown.

It will thus be seen that the objects set forth above, among those elucidated in, or made apparent from, the preceding description, are efficiently attained and, since certain changes may be made in the above construction and/or method without departing from the scope of the invention, it is intended that all matter contained in the above description or shown on the accompanying drawing figures shall be interpreted as illustrative only and not in a limiting sense.

It is also to be understood that the following claims are intended to cover all of the generic and specific features of the invention herein described and all statements of the scope of the invention which, as a matter of language, might be said to fall therebetween.

The embodiments of the invention in which an exclusive property or privilege is claimed are defined as follows:

1. A method of pole-zero correction for digital radiation spectrometers, comprising the steps of:
    (a) setting an analog attenuator;
    (b) sampling and averaging a number of waveforms that contain samples representing preamplifier response before and after a pile-up free detector event and obtaining a discrete waveform therefrom;
    (c) correcting the averaged discrete waveform for DC offset;
    (d) unfolding any known responses of analog and digital networks in the signal chain;
    (e) selecting a portion of the discrete waveform that represents a clean preamplifier response;
    (f) determining if the portion is a straight line;
    (g) if the answer to step (f) is "yes", turning off the pole-zero attenuator;
    (h) if the answer to step (f) is "no", exponentially fitting the discrete preamplifier data and determining the preamplifier time constant; and
    (i) setting the digital pole-zero corrector with parameters corresponding to the preamplifier time constant.

2. Apparatus for pole-zero correction for digital radiation spectrometers, comprising:
    (a) means for setting an analog attenuator;
    (b) means connected to said means for setting to sample and average a number of waveforms that contain samples representing preamplifier response before and after a pile-up free detector event to obtain a discrete waveform therefrom;
    (c) means connected to said means to sample to correct the averaged discrete waveform for DC offset;
    (d) means connected to said means to correct to unfold any known responses of analog and digital networks in the signal chain;
    (e) means connected to said means to unfold to select a portion of the discrete waveform that represents a clean preamplifier response;
    (f) means connected to said means to unfold to determine if the portion is a straight line;
    (g) means connected to said means to unfold to turn off the pole-zero attenuator if the portion is a straight line;
    (h) means connected to said means to unfold to exponentially fit the discrete preamplifier data and to determine the preamplifier time constant; and
    (i) means connected to said means to set the digital pole-zero corrector with parameters corresponding to the preamplifier time constant.

3. A method of pole-zero correction for digital radiation spectrometers with automatic attenuator calibration, comprising the steps of:
    (a) setting an analog attenuator to a digital value;
    (b) sampling and averaging a number of waveforms that contain samples representing the system response before and after a pile-up free detector event and obtaining a discrete waveform therefrom;
    (c) correcting the averaged discrete waveform for DC offset;
    (d) determining if the pulse tail of the discrete waveform is a straight line;
    (e) if the answer to question in step (d) is "yes", turning off the pole-zero attenuator;
    (f) if the answer to the question in step (d) is "no", finding the preamplifier time constant;
    (g) determining if the preamplifier response is a step function;
    (h) if the answer to the question in step (g) is "yes", turning off the pole-zero attenuator;
    (i) if the answer to the question in step (g) is "no", finding the attenuator calibration; and
    (j) calculating the attenuator digital value and setting the attenuator gain.

4. Apparatus for pole-zero correction for digital radiation spectrometers with automatic attenuator calibration, comprising the steps of:
    (a) means to set an analog attenuator to a digital value;
    (b) means connected to said means to set to sample and average a number of waveforms that contain samples representing the system response before and after a pile-up free detector event and to obtain a discrete waveform therefrom;
    (c) means connected to said means to sample to correct the averaged discrete waveform for DC offset;
    (d) means connected to said means to correct to determine if the pulse tail of the discrete waveform is a straight line;
    (e) means connected to said means to correct to turn off the pole-zero attenuator if the pulse tail of the discrete waveform is a straight line;
    (f) means connected to said means to correct to find the preamplifier time constant if the tail of the discrete waveform is not a straight line;
    (g) means connected to said means to find in element (f) to determine if the preamplifier response is a step function;
    (h) means connected to said means to determine to turn off the pole-zero attenuator if the preamplifier response is a step function;
    (i) means connected to said means to determine to find attenuator calibration if the preamplifier response is not a step function; and
    (j) means connected to said means to find in element (i) to calculate the attenuator digital value and set the attenuator gain.

* * * * *

UNITED STATES PATENT AND TRADEMARK OFFICE
CERTIFICATE OF CORRECTION

PATENT NO.    : 6,522,984 B1
DATED         : February 18, 2003
INVENTOR(S)   : Valentin T. Jordanov It is certified that error appears in the above-identified patent and that said Letters Patent is hereby corrected as shown below:

Column 1,
Line 51, should be inserted -- where $\tau_f = C_f R_f$. --

Column 3,
Equation (12) should read  $v_p(t) = \int_0^t I(\lambda)h_p(t-\lambda)d\lambda = \int_0^t I(\lambda)k_p e^{-\frac{t-\lambda}{\tau_p}}d\lambda$ Column 11,
Equation (22) should read  $c = -\frac{1}{D}\frac{\ln(L)\cdot\tau_d}{\ln(L)\cdot\tau_d + T_{clk}}$ Equation (23) should read $$d = \frac{1}{c\left(\frac{\tau_p}{\tau_d}-1\right)} = -D\frac{\ln(L)\cdot\tau_d + T_{clk}}{\ln(L)\cdot(\tau_p - \tau_d)} = -D\frac{\ln(L)\cdot\tau_d + T_{clk}}{\ln(L)\cdot\left(\frac{T_{clk}}{\ln\left(\frac{1+N}{N}\right)} - \tau_d\right)}$$

Equation (24) should read $$d \cong -D\frac{(L-1)\cdot\tau_d + T_{clk}}{(L-1)\cdot(T_{clk}(N-0.5) - \tau_d)}$$

Signed and Sealed this

Twenty-fourth Day of June, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,522,984 B1
DATED : February 18, 2003
INVENTOR(S) : Valentin T. Jordanov It is certified that error appears in the above-identified patent and that said Letters Patent is hereby corrected as shown below:

Column 1,
Line 51, should be inserted -- where $\tau_f = C_f R_f$. --

Column 3,
Equation (12) should read $v_p(t) = \int_0^t I(\lambda) h_p(t-\lambda) d\lambda = \int_0^t I(\lambda) k_p e^{-\frac{t-\lambda}{\tau_r}} d\lambda$ Column 11,
Equation (22) should read $c = -\frac{1}{D} \frac{\ln(L) \cdot \tau_d}{\ln(L) \cdot \tau_d + T_{clk}}$ Equation (23) should read $$d = \frac{1}{c\left(\frac{\tau_p}{\tau_d} - 1\right)} = -D \frac{\ln(L) \cdot \tau_d + T_{clk}}{\ln(L) \cdot (\tau_p - \tau_d)} = -D \frac{\ln(L) \cdot \tau_d + T_{clk}}{\ln(L) \cdot \left(\frac{T_{clk}}{\ln\left(\frac{1+N}{N}\right)} - \tau_d\right)}$$

Equation (24) should read $$d \cong -D \frac{(L-1) \cdot \tau_d + T_{clk}}{(L-1) \cdot (T_{clk}(N-0.5) - \tau_d)}$$

Signed and Sealed this

Eighth Day of July, 2003

JAMES E. ROGAN
*Director of the United States Patent and Trademark Office*